United States Patent [19]

Komiya

[11] 4,311,143
[45] Jan. 19, 1982

[54] APPARATUS FOR RESECTING TISSUE INSIDE THE BODY CAVITY UTILIZING HIGH-FREQUENCY CURRENTS

[75] Inventor: Osamu Komiya, Hachioji, Japan

[73] Assignee: Olympus Optical Co., Ltd., Tokyo, Japan

[21] Appl. No.: 82,932

[22] Filed: Oct. 9, 1979

[30] Foreign Application Priority Data

Oct. 12, 1978 [JP] Japan .................................. 53-125528

[51] Int. Cl.³ .............................................. A61B 17/39
[52] U.S. Cl. ................................................ 128/303.15
[58] Field of Search ........................ 128/303.13–303.17

[56] References Cited

U.S. PATENT DOCUMENTS

| 2,002,559 | 5/1935 | Wappler | 128/303.15 |
| 2,275,167 | 3/1942 | Bierman | 128/303.17 |
| 3,805,791 | 4/1974 | Seuberth et al. | 128/303.14 |
| 3,920,021 | 11/1975 | Hiltebrandt | 128/303.17 |
| 3,938,527 | 2/1976 | Rioux et al. | 128/303.17 |
| 3,955,578 | 5/1976 | Chamness et al. | 128/303.15 |
| 3,982,542 | 9/1976 | Ford et al. | 128/303.14 |
| 4,043,342 | 8/1977 | Morrison, Jr. | 128/303.14 |
| 4,116,198 | 9/1978 | Roos | 128/303.15 |

FOREIGN PATENT DOCUMENTS 2275226  1/1976  France .......................... 128/303.17

*Primary Examiner*—Lee S. Cohen

[57] ABSTRACT

Disclosed is an apparatus for resecting tissue inside the human body cavity by means of high-frequency currents which comprises an electrically insulating elongate tubular sheath, a first electrode exposed at the distal end portion of the sheath, a snare capable of advance and retreat within the sheath and bringing tissue to be resected which is grasped thereby into close contact with the first electrode, the snare constituting a second electrode, the snare constituting a second electrode, a control wire capable of advance and retreat within the sheath and coupled to the snare, whereby the snare is controlled, and a means for supplying high-frequency currents to the snare and the first electrode through the interior of the sheath.

6 Claims, 12 Drawing Figures

APPARATUS FOR RESECTING TISSUE INSIDE THE BODY CAVITY UTILIZING HIGH-FREQUENCY CURRENTS

BACKGROUND OF THE INVENTION

This invention relates to an improvement of apparatus for resecting objective regions inside the body cavity by means of high-frequency currents.

In general, an apparatus for resecting celiac tissue, such as polyps, by means of high-frequency currents employs a system to resect a region inside a body cavity suffering a polyp by applying a high-frequency current between an electrode for resection formed of a looped conductive wire inserted into the body cavity and an external electrode in wide contact with the external surface of the human body which is formed separately from the resection electrode. According to such conventional system, however, the high-frequency current, which is caused to flow through the interior of the body, may bring about cauterization of some other regions of the body than the objective region, frequently causing perforation in unexpected parts of the body or, in case of poor contact between the external electrode and the surface of the body, burns.

Hereupon, there is known an alternative system to apply a high-frequency current between two conductive wires to serve as electrodes of different polarities whose tip ends are coupled to each other with an insulating material between, forming a loop. In this system, however, even if the neck of the polyp is wrung by the loop and supplied with current, the portion touching the insulating material may be left uncauterized, leading to the fear of bleeding. Further, the portion left uncauterized, which may be relatively thick, will possibly not be able to be cut off mechanically.

SUMMARY OF THE INVENTION

Accordingly, the object of this invention is to provide an apparatus capable of preventing leakage of high-frequency currents into the human body and of secure resection of objective regions of the body, despite the simple construction.

In order to attain the above object, an apparatus according to this invention comprises an electrically insulating elongate tubular sheath, a first electrode exposed at the distal end portion of the sheath, a snare means capable of advance and retreat within the sheath and bringing tissue to be resected which is grasped thereby into close contact with the first electrode, the snare means constituting a second electrode, a control wire capable of advance and retreat within the sheath and coupled to the snare means, whereby the snare means is controlled, and a means for supplying high-frequency currents to the snare means and the first electrode through the interior of the sheath.

In the aforementioned apparatus, the snare means is opened outward from the distal end of the sheath by advancing the control wire, and is retreated after grasping the tissue to be resected, so that the tissue is brought into close contact with the first electrode. By applying a high-frequency current between the snare means and the first electrode through the tissue in this state, the tissue may be cauterized and cut off.

DETAILED DESCRIPTION OF THE PREFERRED EMBODIMENTS

Now there will be described several embodiments of this invention with reference to the accompanying drawings.

Figure 1:
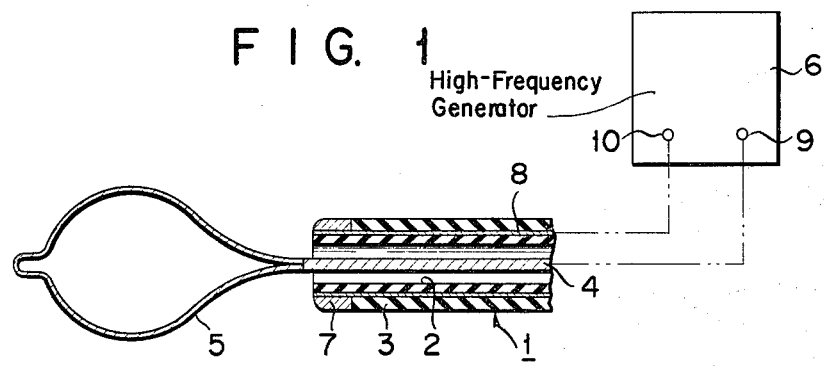
FIG. 1 is a profile of the distal end portion of an apparatus according to a first embodiment of this invention.
Figure 2:
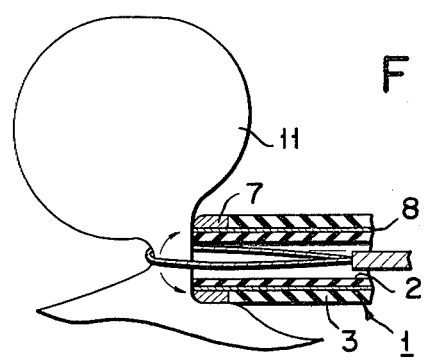
FIG. 2 is a profile of the apparatus of FIG. 1 showing an operating state.

FIGS. 1 and 2 show a first embodiment of the apparatus of this invention. In these drawings, numeral 1 designates an electrically insulating sheath which, consisting of inner and outer tubes 2 and 3, is to be introduced into a body cavity through the channel of an endoscope. A control wire 4, capable of advance and retreat within the sheath 1, is controlled for its movement at the proximal end portion of the sheath 1. A looped snare wire 5 is attached to the distal end of the control wire 4. The snare wire 5 is so urged as to spread out automatically when pushed out from the distal end of the sheath 1, as shown in FIG. 1. Electrically connected with the control wire 4, the snare wire 5 is allowed to communicate with the proximal side of the sheath 1 by means of the control wire 4, and is coupled to a high-frequency generator 6.

At the distal end of the sheath 1, on the other hand, is an exposed electrode 7. The electrode 7 is formed of an annular conductive member, and is fitted and fixed on the outside periphery of the inner tube 2. Further, the electrode 7 is connected with a tubular conductive member 8 interposed between the inner and outer tubes 2 and 3 of the sheath 1, led to the proximal side of the sheath 1, and coupled to the high-frequency generator 6.

Namely, the snare wire 5 and the electrode 7 are connected to terminals 9 and 10 of the high-frequency generator 6, respectively.

In resecting a polyp 11 in the body cavity by using the above-mentioned apparatus, the control wire 4 is previously pulled to keep the snare wire 5 withdrawn in the sheath 1, and the apparatus is introduced into the body cavity through the channel of the endoscope. Thereafter, the control wire 4 is pushed forward to thrust the snare wire 5 out of the sheath 1 through its distal end, thereby allowing the snare wire 5 to spread out automatically, as shown in FIG. 1. Then, the polyp 11 is put in the snare wire 5, when the control wire 4 is pulled toward the proximal side to wring the neck of the polyp 11, as shown in FIG. 2. Then, the high-frequency generator 6 is actuated to let a high-frequency current flow between the snare wire 5 and the electrode 7. The high-frequency current flows only in directions as indicated by the arrows of FIG. 2. Thus, only the portion through which such current flow is passed can be cauterized and cut. Since the high-frequency current never flows through any other regions than the region between the snare wire 5 and the electrode 7, there will be caused no burns or perforation in unrelated or unexpected parts of the body. Moreover, the neck of the polyp 11 can be located entirely between the snare wire 5 and the electrode 7, and the high-frequency current is allowed to flow throughout the neck to enable source resection without causing bleeding attributable to the existence of stumps.

Figure 3:
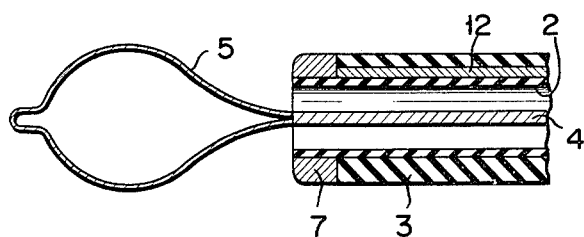
FIG. 3 is a profile of the distal end portion of an apparatus according to a second embodiment.
Figure 4:
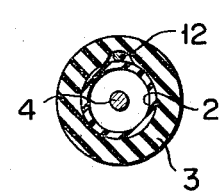
FIG. 4 is a cross-sectional view of the apparatus of FIG. 3.
Figure 5:
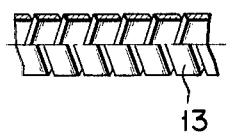
FIGS. 5 and 6 are partially broken profiles of conductive members for supplying high-frequency currents to a first electrode.
Figure 6:
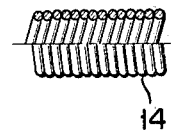

It is to be understood that this invention is not limited to the aforementioned precise embodiment, and that various changes and modifications may be effected herein by one skilled in the art. According to a second embodiment of the invention as shown in FIGS. 3 and 4, an electric wire 12 is used for the conductive member in the sheath 1. FIGS. 5 and 6 show, respectively, a conductive band 13 and an electric wire 14 which are to be alternatively wound round the inner tube (not shown). Said conductive band 13 and electric wire 14 are used for the conductive member in the sheath 1.

Figure 7:
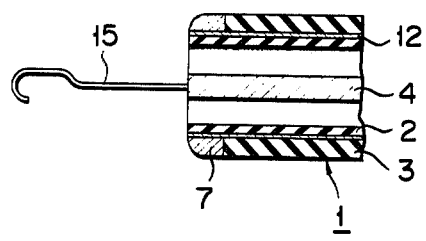
FIG. 7 is a profile of the distal end portion of an apparatus according to a third embodiment.
Figure 8:
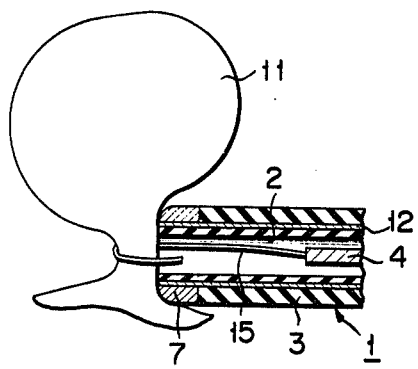
FIG. 8 is a profile of the apparatus of FIG. 7 showing an operating state.

FIG. 7 shows a third embodiment of the invention, in which a snare hook 15 is used in place of the snare wire 5. According to this embodiment, the neck of the polyp 11 can be hooked even though it is too massive for the loop of the snare wire 5. Namely, polypectomy can be performed independently of the size of the neck of the polyp 11. FIG. 8 shows a state in which the snare hook 15, engaged with the neck of the polyp 11, is drawn in.

Figure 9:
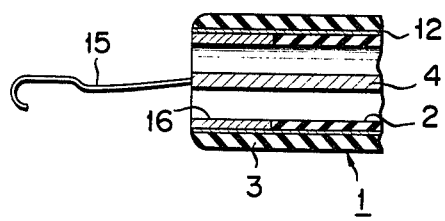
FIG. 9 is a profile of the distal end portion of an apparatus according to a fourth embodiment.
Figure 10:
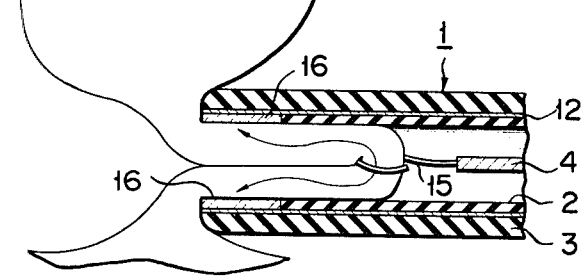
FIG. 10 is a profile of the apparatus of FIG. 9 showing an operating state.

FIG. 9 shows a fourth embodiment of the invention, in which an electrode 16 is exposed on the inside of the sheath 1 at the distal end thereof. That is, the electrode 16 is an annular conductive member fitted in and fixed to the inside of the outer tube 3 of the sheath 1. When using the apparatus furnished with the snare hook 15, for example, the neck of the polyp 11 is caught by the snare hook 15 and drawn into the distal end portion of the sheath 1 to provide a state shown in FIG. 10. Then, a high-frequency current is applied between the snare hook 15 and the electrode 16. Thus, the high-frequency current flows in the directions of the arrows in FIG. 10, so that the neck of the polyp 11 may be cauterized.

Figure 11:
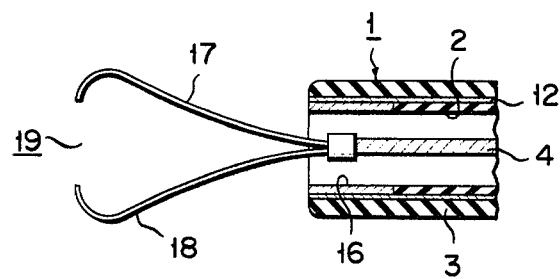
FIG. 11 is a profile of the distal end portion of an apparatus according to a fifth embodiment.
Figure 12:
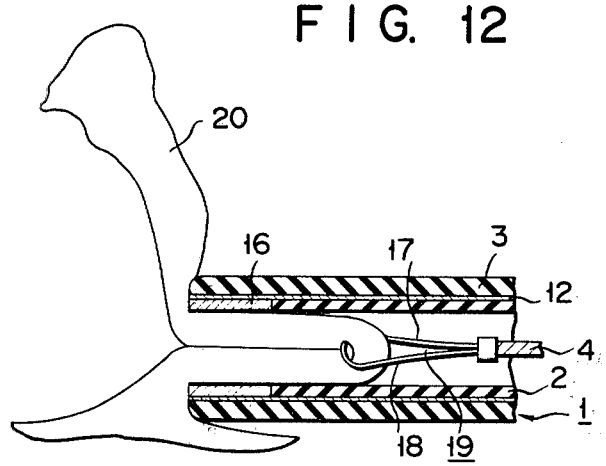
FIG. 12 is a profile of the apparatus of FIG. 11 showing an operating state.

Further, FIGS. 11 and 12 show a fifth embodiment of the invention, in which a snare 19 composed of a pair of grab levers 17 and 18 is used in place of the snare hook 15 of the preceding embodiment. Also in these drawings, the region to be cauterized is being drawn into the sheath 1. FIG. 12 shows how a Fallopian tube 20, for example, is drawn in.

In connection with the above description of the embodiments of the invention, like reference numerals refer to the same parts throughout the several views of the drawings.

According to this invention, as described above, a high-frequency current is caused to flow between the snare means to grasp tissue to be resected and the first electrode exposed at the distal end portion of the sheath, and the current flows through the tissue held at the distal end portion of the sheath, thereby cauterizing the tissue. Namely, it is made possible to inhibit the high-frequency current from leaking to other regions of the human body than the objective region, thereby preventing burning of such objective region. Furthermore, the high-frequency current is allowed to flow between the snare means and the first electrode, so that the objective region can be resected, so to speak, completely without leaving any stump and hence without involving bleeding or any other trouble.

What is claimed is:

1. An apparatus for resecting tissue inside the human body cavity by means of high-frequency currents, comprising:
   an electrically insulating elongate tubular sheath having a distal end;
   a first electrode exposed adjacent said distal end of said sheath;
   a snare means capable of advance out of said sheath and retreat completely within said sheath and spaced from said sheath distal end inwardly of said sheath for bringing tissue to be resected which is grasped thereby into close contact with said first electrode; said snare means constituting a second electrode;
   a control wire extending through said sheath and capable of advance out of and retreat into said sheath and coupled to said snare means, whereby said snare means is moved out of and completely into said sheath; and
   a means for supplying high-frequency currents to said snare means and said first electrode through the interior of said sheath.

2. An apparatus according to claim 1, wherein said first electrode is disposed on the outside of the distal end portion of said sheath.

3. An apparatus according to claim 1, wherein said first electrode is disposed on the inside of the distal end portion of said sheath.

4. An apparatus according to any one of claims 1 to 3, wherein said snare means is formed of a looped wire.

5. An apparatus according to any one of claims 1 to 3, wherein said snare means is formed of a hooked wire.

6. An apparatus according to any one of claims 1 to 3, wherein said snare means is composed of a pair of grab levers.

* * * * *